United States Patent [19]

König et al.

[11] 4,107,200

[45] Aug. 15, 1978

[54] BIS(AMINOPROPYL) ARYLACETONITRILES AND PREPARATION THEREOF

[75] Inventors: Eberhard König, Leverkusen; Josef Pedain, Cologne, both of Germany

[73] Assignee: Bayer Aktiengesellschaft, Leverkusen, Germany

[21] Appl. No.: 763,218

[22] Filed: Jan. 27, 1977

[30] Foreign Application Priority Data

Feb. 7, 1976 [DE] Fed. Rep. of Germany ....... 2604794

[51] Int. Cl.$^2$ ............................................. C07C 121/78
[52] U.S. Cl. ...................... 260/465 E; 260/29.2 TN; 260/465 H; 260/858; 528/68
[58] Field of Search ................................... 260/465 E

[56] References Cited

U.S. PATENT DOCUMENTS

| | | | |
|---|---|---|---|
| 2,510,784 | 6/1950 | Lucas | 260/465 |
| 3,661,918 | 5/1972 | Bouboulis | 260/293.52 |

OTHER PUBLICATIONS

Badger et al., J. Chem. Soc., pp. 1141–1144 (1949).

*Primary Examiner*—Dolph H. Torrence
*Attorney, Agent, or Firm*—Gene Harsh; Joseph C. Gil; R. Brent Olson

[57] ABSTRACT

This invention relates to new aliphatic diamines containing cyanide groups, a process for their preparation by hydrogenation of the corresponding trinitriles and their use as chain lengthening agents in the isocyanate polyaddition process.

10 Claims, No Drawings

BIS(AMINOPROPYL) ARYLACETONITRILES AND PREPARATION THEREOF

BACKGROUND OF THE INVENTION

It is known that 2 molecules of acrylonitrile can be added to aryl substituted acetonitriles. As described by Bruson and Reiner in J.Amer.Chem.Soc. 64. 2850 (1942) and U.S. Pat. No. 2,305,529, the reaction proceeds smoothly and in high yields to trinitrile compounds of the general formula $$\text{Ar}-\underset{\underset{CH_2-CH_2-C\equiv N}{|}}{\overset{\overset{CH_2-CH_2-C\equiv N}{|}}{C}}-C\equiv N$$

It is also known from a publication by Badger et al. in J.Chem.Soc. 1949, 1141-4, that hydrogenation of such trinitrile compounds may lead to cyclized products or decomposition products, e.g. 3-phenyl-piperidine, ammonia and other, unidentified high melting basic compounds.

U.S. Pat. No. 3,661,918, however, describes the formation of a bicyclic tertiary amine compound of the formula $$C_6H_5-\underset{\underset{CH_2}{|}}{\overset{\overset{CH_2}{|}}{C}}\underset{CH_2}{\overset{CH_2}{\diagdown}}\underset{CH_2}{\overset{CH_2}{\diagup}}N$$

which is obtained from the above phenyl substituted trinitrile compound by varying the hydrogenation conditions.

All the above mentioned hydrogenation products are thus either secondary or tertiary amines.

The amino compounds mentioned above are not suitable for the production of high molecular weight synthetic resins by the isocyanate addition process which mainly requires difunctional components.

It has now surprisingly been found that the above mentioned trinitriles can be hydrogenated in such a way that new diamines are obtained in high yields. These new diamines still contain an unchanged nitrile group. Because of the presence of this nitrile group, the new diamines are suitable for the production of nitrile-containing polyurethane ureas or polyureas by the isocyanate polyaddition process. The nitrile-containing polyaddition products obtained using the new diamines as chain lengthening agents are distinguished by numerous remarkably advantageous properties, in particular their excellent adherence to a variety of substrates and their exceptional oil resistance.

SUMMARY OF THE INVENTION

The present invention, thus, relates to compounds of the formula $$H_2N-H_2C-\underset{}{\overset{\overset{R}{|}}{HC}}-H_2C-\underset{\underset{C\equiv N}{|}}{\overset{\overset{Ar}{|}}{C}}-CH_2-\underset{}{\overset{\overset{R}{|}}{CH}}-CH_2-NH_2$$

in which

Ar represents an aromatic hydrocarbon group having from 6 to 14 carbon atoms and which may carry one or more substituents which are inert towards amino groups and R represents hydrogen or an aliphatic hydrocarbon group having from 1 to 4 carbon atoms.

The present invention also relates to a process for the preparation of these new compounds, characterized in that the trinitriles of the formula $$N\equiv C-\underset{}{\overset{\overset{R}{|}}{CH}}-CH_2-\underset{\underset{C\equiv N}{|}}{\overset{\overset{Ar}{|}}{C}}-CH_2-\underset{}{\overset{\overset{R}{|}}{CH}}-C\equiv N$$

in which

Ar and R have the meaning indicated above, are hydrogenated in solvents or solvent mixtures containing at least about 80% by weight of one or more weakly polar or non-polar organic solvents, at temperatures below about 130° C and in the presence of hydrogenation catalysts.

Finally, the invention relates to the use of the new diamines as chain lengthening agents in the production of polyurethane ureas or polyureas by the isocyanate polyaddition process.

DETAILED DESCRIPTION OF THE INVENTION

The trinitriles to be used in the process according to the invention are obtainable according to U.S. Pat. No. 2,305,529, incorporated herein by reference, from arylacetonitriles of the formula $$Ar-CH_2-C\equiv N$$

and acrylonitriles of the formula $$CH_2=\underset{}{\overset{\overset{R}{|}}{C}}-C\equiv N$$

in which formula, as well as in the preceding and following formula,

Ar represents an aromatic hydrocarbon group having from 6 to 14 carbon atoms, preferably a phenyl group, which may be substituted by one or more substituents which are inert towards amino groups, and R represents hydrogen or an aliphatic hydrocarbon group having from 1 to 4 carbon atoms, preferably hydrogen or a methyl group and most preferably hydrogen.

Possible substituents on the group Ar include in particular halogen, preferably chlorine, $C_1$ to $C_4$ alkyl, preferably methyl, or $C_1$ to $C_4$ alkoxy, preferably methoxy groups.

Examples of suitable arylacetonitriles include phenylacetonitrile, naphthylacetonitrile, 4-chlorophenylacetonitrile and 4-methoxyphenylacetonitrile. Phenylacetonitrile is preferred.

Examples of suitable acrylonitriles include acrylonitrile, methacrylonitrile, ethyl-acrylonitrile and butylacrylonitrile. Acrylonitrile and methacrylonitrile are preferred, particularly acrylonitrile.

The groups Ar and R in the compounds according to the invention are the same as the corresponding groups Ar and R in the above mentioned starting compounds.

When carrying out the process according to the invention, the trinitriles of the following formula prepared from the aforesaid starting materials:

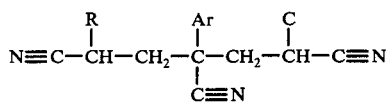

in which

Ar and R have the meaning indicated above, are dissolved in an organic solvent or a mixture of several organic solvents. The concentration of the solution should be between about 15 and 40% by weight. At least about 80% by weight of the solvent or solvent mixture should consist of a weakly polar or non-polar organic solvent, that is to say a solvent with a dielectric constant (DIN 53483) below about 7.

The following are examples of such solvents:

Aromatic hydrocarbons, which may be alkyl substituted, e.g. benzene, toluene, ethylbenzene, o-, m- or p-xylene, chlorobenzene or anisole; aliphatic and cycloaliphatic hydrocarbons such as octane, nonane, and decane and their isomers, cyclohexane, methylcyclohexane, ethylcyclohexane and dimethylcyclohexane as well as commercial solvent mixtures having a dielectric constant below about 7, such as the usual commercial petroleum ethers. Aromatic hydrocarbons are preferred.

The solvent mixtures used in the process according to the invention may contain up to about 20% by weight, preferably about 0 to 10% by weight of polar solvents, i.e. solvents with dielectric constants (DIN 53483) above about 7.

Examples of such solvents include methanol, ethanol, propanol and their higher homologues as well as araliphatic alcohols, e.g. benzyl alcohol.

It is preferred to carry out the process without the addition of polar solvents. Hydrogenation of the starting compounds is carried out by known methods using hydrogen, preferably with the addition of ammonia, in an autoclave. According to the invention, the reaction temperature should not exceed about 130° C and is preferably maintained between about 80° and 130° C. The reaction proceeds particularly smoothly and in high yields at a temperature of from about 100° to 120° C.

The autoclave pressure during hydrogenation is preferably maintained at about 120 to 200 bar, in particular 140 to 170 bar.

Hydrogenation is preferably carried out in the presence of a catalyst. Raney cobalt and Raney nickel are suitable hydrogenation catalysts. Other catalysts based on platinum or palladium may in principle also be used but Raney cobalt is preferred.

The solutions of diamines according to the invention obtained as described above may be freed from hydrogenation catalyst by filtration and then used in this form for various purposes; for example they may be worked up into solutions of the corresponding isocyanates by known methods. Also, the solvents may be removed by distillation, the diamines according to the invention then being left behind as pale yellow, low viscosity liquids. It is a particular advantage of the process according to the invention that the diamines are obtained in a highly pure state very suitable for commercial purposes and do not require the usual processes of purification by distillation or chromatography.

The diamines according to the invention are eminently suitable for use as chain lengthening agents for the production of lightfast polyurethane elastomers or polyurea elastomers. They are also valuable components for the formation of polyamides and for hardening polyepoxides.

When the diamines according to the invention are used as chain lengthening agents, they may be used instead of or as mixtures with the chain lengthening agents conventionally used in polyurethane chemistry. One possible use of the new diamines, and one which is preferred according to the present invention, is as chain lengthening agents in the preparation of aqueous polyurethane dispersions. For this purpose, prepolymers containing free isocyanate groups are reacted with aqueous solutions of the diamines according to the invention. Polyurethane polyureas and polyureas produced with the aid of the new diamines are distinguished by their excellent adherence to any substrates and exceptionally high oil resistance.

The following Examples serve to explain the invention more fully without restricting it.

EXAMPLES

PREPARATION OF STARTING COMPOUNDS

EXAMPLE 1

3-Phenyl-pentane-1,3,5-tricarboxylic acid trinitrile may be prepared either as described by Bruson and Riener in J.Amer.Chem.Soc. 65, 23 (1943) or as follows: 450 g (8.5 mol) of acrylonitrile are added dropwise to a mixture of 468 g (4 mol) of benzyl cyanide, 14 g of potassium hydroxide (3%), 240 ml of dioxane and 160 ml of water at room temperature with stirring and at such a rate that the temperature is maintained at 30° to 35° C, if necessary with cooling. Stirring is then continued for a further 2 hours to complete the reaction. The crystalline paste is acidified, diluted with methanol/water, suction filtered and dried. 840 g (94% of the theory) of colorless crystals melting at 70° C are obtained.

EXAMPLE 2

3-(4-Chloro-phenyl)-pentane-1,3,5,-tricarboxylic acid trinitrile 212 g (4 mol) of acrylonitrile are added dropwise to a mixture of 302 g (2 mol) of 4-chlorophenylacetonitrile, 10 g of potassium hydroxide, 400 ml of dioxane and 20 ml of water at 40° C with stirring at such a rate that the temperature is maintained at 40° to 45° C. Stirring is continued for 6 hours at room temperature after all the acrylonitrile has been added. The crystalline paste which precipitates is acidified with dilute hydrochloric acid suction filtered, washed with methanol and dried. 450 g (87% of the theory) of colorless crystals, m.p. 122° C, are obtained.

PROCESS ACCORDING TO THE INVENTION

EXAMPLE 3

4-Amino-1-aminopropyl-1-phenyl-butane carboxylic acid nitrile.

1800 g of the trinitrile compound prepared according to Example 1 are hydrogenated in 4500 ml of toluene to which 500 g of liquid ammonia are added, hydrogenation being carried out in a 10 liter autoclave in the presence of 200 g of Raney cobalt at 115° C and a pressure of 150 bar until uptake of hydrogen is completed. After removal of the catalyst by filtration and concentration of the hydrogenated solution by evaporation under a vacuum of 14 Torr, a pale yellow oil is left behind. According to gas chromatographic determination, this oil contains the desired diamine in a degree of purity of 96%. The constitution of this diamine is confirmed by its IR, NMR and mass spectrum and by GC-MS coupling and quantitative analysis:

$C_{14}H_{21}N_3$ (Mw 231) Calculated: C 73.0 H 9.1 W 18.2 Found 72.7 9.1 18.0

EXAMPLE 4

4-Amino-1-aminopropyl-1-phenyl-butane carboxylic acid nitrile (see Example 3)

600 g of the trinitrile compound prepared according to Example 1 are hydrogenated in a mixture of 1100 ml of cyclohexane, 100 ml of methanol and 250 g of ammonia in a 3 liter autoclave in the presence of 70 g of Raney cobalt at 110° C and a pressure of 170 bar until uptake of hydrogen is completed. The reaction mixture is then worked up as described in Example 3. The diamine is obtained as a pale yellow oil which is 98% pure.

EXAMPLE 5

(Comparison Example)

4a-Phenyl-1,2,3,4,4a, 5,6,7-tetrahydro-1,8-naphthryridine

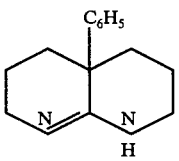

600 g of the trinitrile compound prepared according to Example 1 are hydrogenated in 1100 ml of methanol and 200 g of ammonia in a 3 liter autoclave in the presence of 70 g of Raney cobalt at 150° C and a pressure of 150 bar until uptake of hydrogen is completed. The products obtained after working up the reaction mixture as described in Example 3 is a solid which recrystallizes from methanol to yield 400 g (70% of the theory) of colorless crystals melting at 152° C.

The constitution of this amine is confirmed by its IR, NMR and mass spectrum.

EXAMPLE 6

4-Amino-1-aminopropyl-1-(4-chlorophenyl)-butane carboxylic acid nitrile 500 g of the trinitrile compound prepared according to Example 2 are hydrogenated in 1400 ml of toluene and 200 g of ammonia in a 3 liter autoclave in the presence of 65 g of Raney cobalt at 115° C and a pressure of 150 bar until uptake of hydrogen is completed. After removal of the catalyst by filtration and concentration of the hydrogenated solution by evaporation under vacuum of 14 Torr at 90° C, a pale yellow oil is left behind.

According to gas chromatographic determination, this oil contains the desired diamine in a degree of purity of $C_{14}H_{20}N_3Cl$ (Mw 265).

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. Compounds of the formula

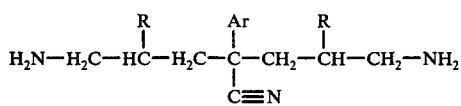

in which
Ar represents an aromatic hydrocarbon group having from 6 to 14 carbon atoms, which may carry one or more substituents which are inert towards amino groups and
R represents hydrogen or an aliphatic hydrocarbon group having from 1 to 4 carbon atoms.

2. Compounds of the formula according to claim 1, in which Ar represents a phenyl group and R represents hydrogen or a methyl group.

3. Process for the preparation of compounds according to claim 1, characterized in that trinitriles of the formula

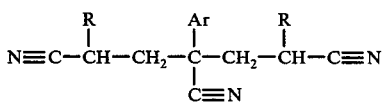

in which
Ar and R have the meaning indicated in claim 1, are hydrogenated in solvents or solvent mixtures which consist to an extent of at least about 80% by weight of one or more weakly polar or non-polar organic solvents, at temperature below about 130° C and in the presence of hydrogenation catalysts.

4. The process of claim 3 wherein the weakly polar or non-polar solvents have a dielectric constant below about 7.

5. The process of claim 4 wherein the weakly polar or non-polar solvents are selected from the group consisting of aromatic hydrocarbons, aliphatic and cycloaliphatic hydro carbons and commercial solvent mixtures 6. The process of claim 5 wherein the weakly polar or non-polar solvents are aromatic hydrocarbons.

7. The process of claim 5 wherein the weakly polar or non-polar organic solvents are selected from the group consisting of benzene, toluene, ethylenebenzene, o-xylene, m-xylene, p-xylene, chlorobenzene, anisole, octane, nonane, decane, isomers of octane, nonane and decane, cyclohexane, methylcyclohexane, ethylcyclohexane, dimethylcyclohexane and commercial petroleum ethers having a dielectric constant below about 7.

8. The process of claim 3 wherein the solvents or solvent mixtures contain at most about 20% by weight of polar solvents having a dielectric constant above about 7.

9. The process of claim 8 wherein the polar solvents are selected from the group consisting of methanol, ethanol, propanol and benzyl alcohol.

10. The process of claim 3 wherein the hydrogenation catalyst is selected from the group consisting of Raney cobalt and Raney nickel.

* * * * *